United States Patent [19]
Zaleski

[11] Patent Number: 5,242,449
[45] Date of Patent: Sep. 7, 1993

[54] OPHTHALMIC INSTRUMENT
[75] Inventor: Edward R. Zaleski, Santa Ana, Calif.
[73] Assignee: Allergan, Inc., Irvine, Calif.
[21] Appl. No.: 869,630
[22] Filed: Apr. 16, 1992

Related U.S. Application Data
[63] Continuation-in-part of Ser. No. 690,808, Apr. 3, 1991.
[51] Int. Cl.$^5$ .............................................. A61M 1/00
[52] U.S. Cl. ..................................... 606/107; 604/22; 604/35; 604/281; 604/902
[58] Field of Search .................. 606/1, 107, 169, 171; 604/22, 35, 280, 281, 27, 902

[56] References Cited
U.S. PATENT DOCUMENTS

| | | | |
|---|---|---|---|
| 3,782,381 | 1/1974 | Winnie | 604/281 |
| 3,994,297 | 11/1976 | Kopf | 606/107 |
| 4,063,557 | 12/1977 | Wuchinich et al. | |
| 4,068,659 | 1/1978 | Moorehead | 604/280 |
| 4,530,359 | 7/1985 | Helfgott et al. | |
| 4,553,957 | 11/1985 | William et al. | 604/902 |
| 4,570,632 | 2/1986 | Woods | |
| 4,655,743 | 4/1987 | Hyde | 604/22 |
| 4,705,500 | 11/1987 | Reimels et al. | 604/35 |
| 4,766,897 | 8/1988 | Smirmaul | |
| 5,084,012 | 1/1992 | Kelman | 604/35 |
| 5,154,694 | 10/1992 | Kelman | 606/107 |
| 5,154,696 | 10/1992 | Shearing | 604/22 |

FOREIGN PATENT DOCUMENTS
WO9002536 3/1990 PCT Int'l Appl. .

*Primary Examiner*—Stephen C. Pellegrino
*Assistant Examiner*—Glenn K. Dawson
*Attorney, Agent, or Firm*—Poms, Smith, Lande & Rose

[57] ABSTRACT

An ophthalmic instrument having an elongated tube having proximal and distal end portions, a distal end and an elongated passage opening at a distal opening at the distal end. The distal end portion is sized to be received through an incision into the eye. An elongated member having a resiliently deformable end portion is at least partially received in the elongated passage of the tube. The distal end portion of the inner member has a curved configuration in a relaxed condition and is capable of performing a function within the eye. The tube and the inner member are relatively movable longitudinally so that the distal end portion of the inner member can be caused to project through the distal opening a variable amount to change the length of the arc of the curved configuration projecting from the distal opening. A hollow ultrasound needle is positioned in the inner member which is movable relative to the needle.

14 Claims, 9 Drawing Sheets

OPHTHALMIC INSTRUMENT

This application is a continuation-in-part of U.S. patent application Ser. No. 07/690,808, filed Apr. 3, 1991 for Ophthalmic Instrument.

BACKGROUND OF THE INVENTION

1. Field of the Invention

This invention relates to ophthalmic instruments and more particularly to instruments which are usable to irrigate and aspirate the eye during surgery and/or to ultrasonically remove the natural lens from the eye.

2. Background of the Invention

During ophthalmic surgery, it is often necessary to perform various functions within the eye. For example, during cataract surgery, these functions include breaking up of the natural lens of the eye, irrigating the eye and aspirating the natural lens particles and irrigation fluid from the eye. Examples of other functions that it may be desirable to carry out in the eye include viewing the interior of the eye and using laser energy within the eye.

To carry out these and other functions within the eye, it is necessary to make an incision in the eye. To minimize trauma and to speed the healing process, it is desirable that the incision be as small as possible. The ophthalmic instrument is then inserted through the incision into the interior of the eye. Once inserted, it is desirable to limit movement of the instrument at the sclera and the posterior capsule to calm the eye. Unfortunately, restricting movement of the instrument within the eye is often inconsistent with the task which that instrument must perform. In addition, the function to be performed may require movement of the tip of the instrument to various different locations in the eye, some of which are relatively inaccessible.

SUMMARY OF THE INVENTION

This invention provides an ophthalmic instrument which can be inserted through a small incision into the eye and, once inserted, can perform various functions within the eye. With this invention, work can be performed at various different locations within the eye without moving the portion of the instrument which contacts the sclera or, if desired, the entrance to the posterior capsule. Consequently, the necessary functions can be performed through a small incision, and the eye is allowed to remain more calm. In addition, because the small incision may fit relatively tightly around the instrument, fluid loss from the eye is minimized.

The invention can be embodied in an ophthalmic instrument which includes an elongated tube having proximal and distal end portions, a distal end and an elongated passage opening at a distal opening at the distal end. The distal end portion of the tube is sized to be received through an incision into the eye, and this incision may be relatively small.

The ophthalmic instrument also includes an elongated inner member which has a resiliently deformable distal end portion which has a curved configuration in its relaxed condition. The resiliently deformable distal end portion is sized to be received through an incision into the eye and is capable of performing a function or functions within the eye. The inner member is at least partially received in the elongated passage of the tube.

This construction provides a number of advantages. For example, the distal end portion of the tube and the inner member are relatively movable longitudinally so that the distal end portion of the inner member can be caused to project through the distal opening of the tube a variable amount. This changes the length of the arc of the curved configuration which projects from the distal opening to permit the distal end portion of the inner member to do its work at various different locations within the eye without having to move the tube relative to the eye. Viewed from another perspective, this relative movement is between a first position in which the distal end portion of the inner member is retracted into the distal end portion of the tube and a second position in which the distal end portion of the inner member projects outwardly through the distal opening. Means is provided for causing this relative movement between the distal end portion of the tube and the inner member. Such means may take many different forms and may, if desired, include a motor for causing or imparting this relative movement. Alternatively, the relative motion can be accomplished manually.

In addition, by allowing the distal end portion of the tube and inner member to be relatively rotatable, the distal end portion can perform its work within the eye through whatever angle the tube and inner member are rotated. This permits the distal end portion of the inner member to reach many other regions of the eye. By rotating the inner member, the tube can be held stationary relative to the critical regions of the eye.

An important feature of the invention is that the distal end portion of the inner member has a curved configuration in a relaxed condition and that it is resiliently deformable. Because of this construction, withdrawing of the distal end portion partially within the distal opening of the tube automatically reduces the length of the arc of the curved configuration. Also, for insertion of the instrument, the inner member can be withdrawn completely within the tube. The tube is preferably linear so that it can be passed through a small incision into the eye. Once within the eye, the inner member can be extended distally from the distal opening to the length desired, and with such projecting length being in the form of an arc to provide increased coverage. Although the maximum arc of the curved configuration can be of any desired length, preferably the maximum arc is at least about 180 degrees in the relaxed condition and optimally is about 250 degrees.

The distal end portion of the inner member can be of various different materials, such as a resiliently deformable elastomeric or polymeric material with silicone being preferred. Alternatively, a laminate of elastomeric and polymeric materials could be used. Other arrangements, such as the use of a resilient or nonresilient material having a resilient wire embedded therein can also be employed.

Because the inner member is a primary function performer of the instrument within the eye, it is often desirable to utilize a tubular inner member. This enables the inner member to be used, for example, for aspiration or irrigation or to carry another member, such as optical fibers which may be used for illumination, visualization of the interior of the eye or transmission of laser energy.

Preferably, there is a gap between the tube and the inner member. This gap provides a fluid path, and although this fluid path can be used for different purposes, it is particularly suited for irrigation fluid.

Another important function that the instrument may be used to carry out is ultrasonically breaking up the nucleus of the natural lens. For this purpose, the instrument may include an elongated ultrasound needle in the passage of the inner member and means, such as an ultrasound horn, for imparting ultrasonic energy to the ultrasound needle. The distal end portion of the ultrasound needle projects out of the distal opening of the tube, and the inner member and the tube are relatively movable longitudinally between a first position in which the distal end portion of the inner member extends distally of the distal end portion of the ultrasound needle and a second position in which the distal end portion of the ultrasound needle projects distally of the distal end of the inner member. This enables the ultrasound needle to be used without interference from the curved distal end portion of the inner member and, conversely, permits the curved distal end portion of the inner member to be used, for example, for aspiration purposes at various inaccessible regions of the eye without inference from the ultrasound needle.

The ultrasound needle has an elongated needle passage opening at a distal end of the needle, which can desirably be used for aspiration purposes. An optional, but desirable, feature of this invention is that the needle passage is of progressively increasing cross-sectional area as the needle passage extends proximally. This reduces the likelihood that particles being aspirated through the needle passage will become lodged in the needle passage and obstruct it.

The features of this invention are preferably embodied in an ophthalmic instrument in which the tube forms a handpiece. The handpiece preferably has a first proximal opening which is located proximally of the distal end portion and which communicates with the elongated passage in the inner member. Consequently, by applying suction to this proximal opening, the inner member can be used for aspiration. The handpiece may also have a second proximal opening located proximally of the distal end portion of the handpiece, and the fluid path between the inner member and the handpiece communicates with the second proximal opening. This enables the supply of an irrigation fluid through the second proximal opening to the fluid path.

Flexible conduits may be employed to couple the proximal openings of the handpiece to a vacuum source and a source of irrigation fluid. The handpiece includes features which enable rotation of one portion or section of the handpiece relative to the portion or section containing the proximal openings so as to reduce the likelihood of tangling or twisting the flexible conduits. Also, the handpiece has features which allow communication between the fluid path and the second proximal opening at a plurality of different angular positions of the handpiece sections. Similarly, the instrument preferably includes a seal between the inner member and a portion of the handpiece which seals the instrument against leaks in either the irrigation or aspiration flowpaths at different relative angular positions of the relatively rotatable handpiece sections and at different relative axial positions of the inner member and the handpiece.

The invention, together with additional features and advantages thereof, may best be understood by reference to the following description taken in connection with the accompanying illustrative drawings.

DESCRIPTION OF THE PREFERRED EMBODIMENT

FIGS. 1-6 show an ophthalmic instrument which generally comprises an elongated tube in the form of a handpiece 13 having an elongated passage 15 opening at a distal opening 17 at the distal end 19 (FIGS. 2A and 6) and an elongated inner member 21 at least partially received in the passage 15. Although the handpiece 13 can be of various different constructions, in this embodiment, the passage 15 extends axially from the distal end 19 to a first proximal opening 23 (FIG. 2) which is located at a proximal end 25 of the handpiece.

Figure 1:
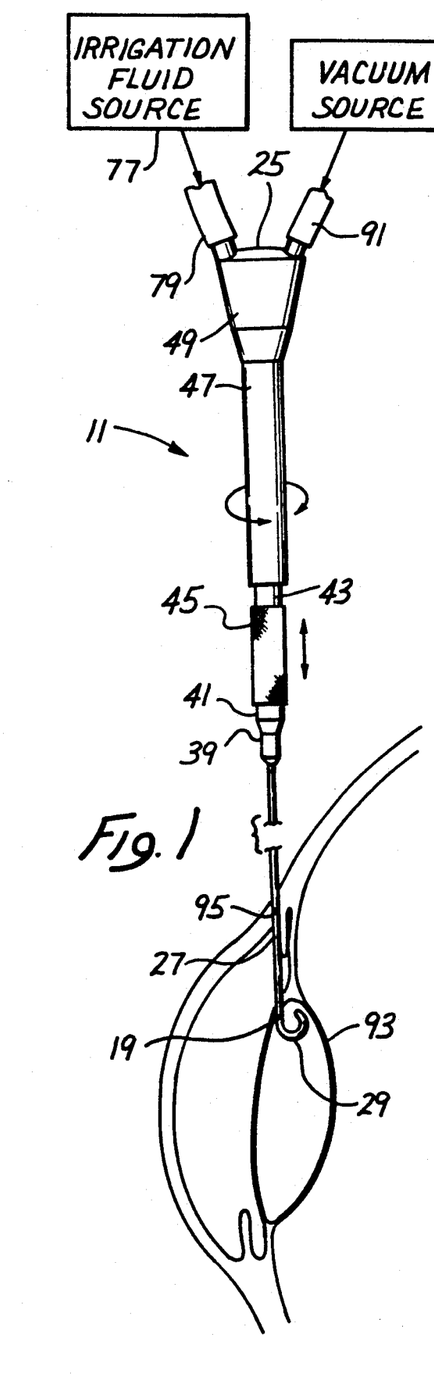
FIG. 1 is an elevational view, partially in section, illustrating an ophthalmic instrument constructed in accordance with the teachings of this invention being employed within the eye.
Figure 2:
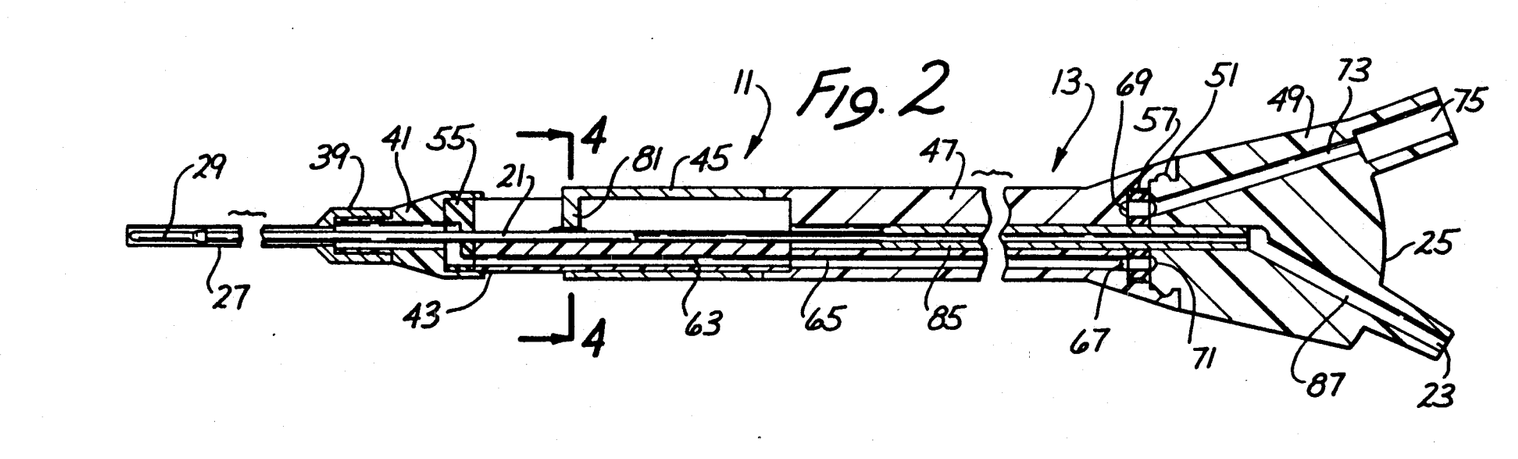
FIG. 2 is a longitudinal sectional view of one form of ophthalmic instrument of this invention with the distal end portion of the inner member fully retracted within the handpiece.
Figure 2A:
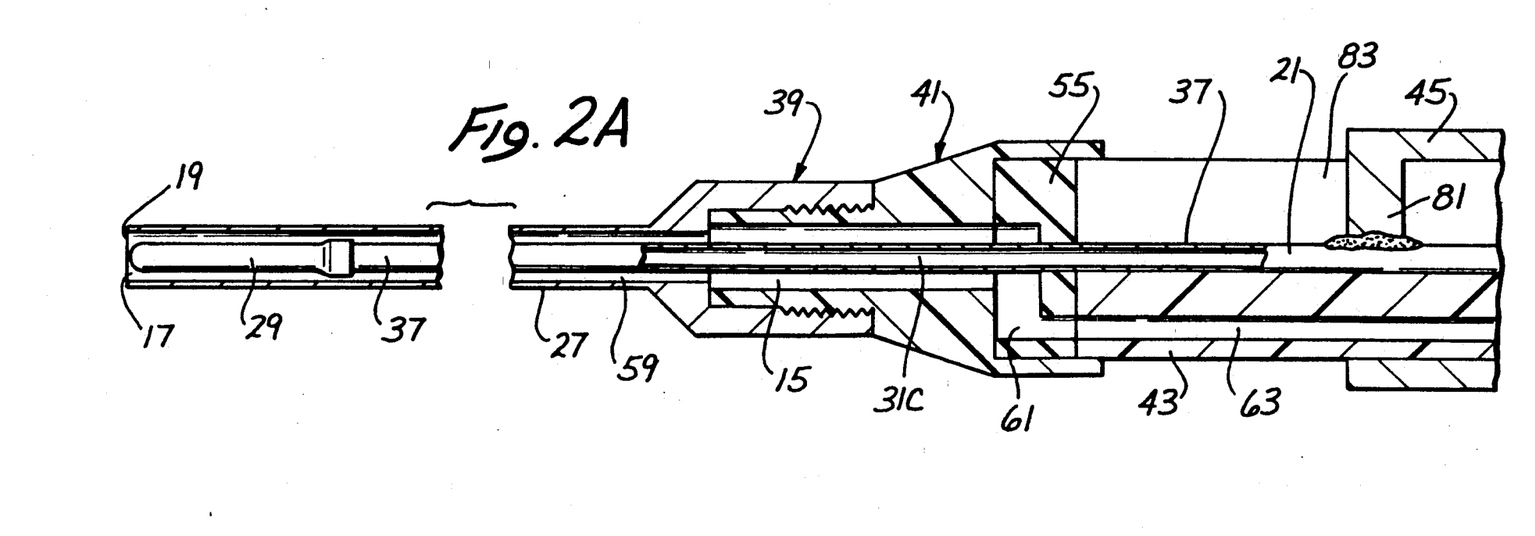
FIG. 2A is an enlarged, fragmentary sectional view showing a portion of the instrument of FIG. 2.

The handpiece includes a distal end portion 27 which is sized to be received through an incision into the eye (FIGS. 1-2A). As such, the distal end portion 27 is preferably in the form of a right circular cylinder, and the passage 15, which is preferably cylindrical, extends axially through the distal end portion 27.

Figure 6:
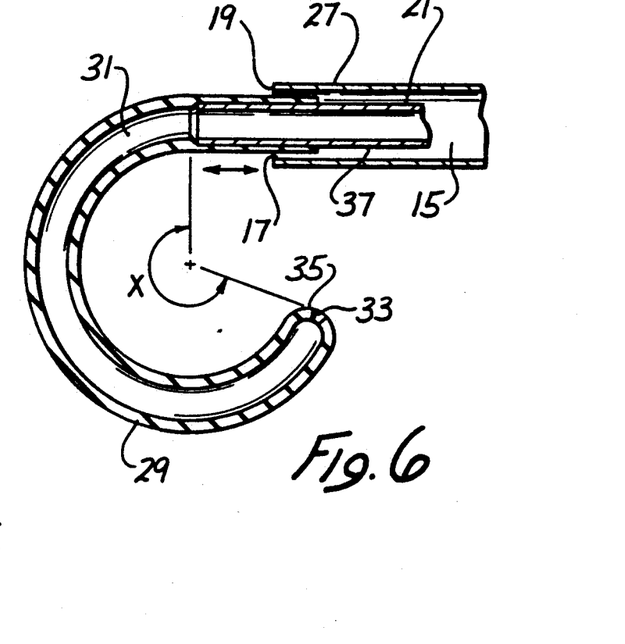
FIG. 6 is an enlarged, fragmentary, sectional view showing the distal regions of the ophthalmic instrument with the distal end portion of the inner member extended.

The inner member 21 has a resiliently deformable distal end portion 29 which has a curved configuration in a relaxed condition as best seen in FIG. 6. The distal end portion 29 is also sized to be received through an incision into the eye, and it is capable of performing one or more functions within the eye.

Figure 6A:
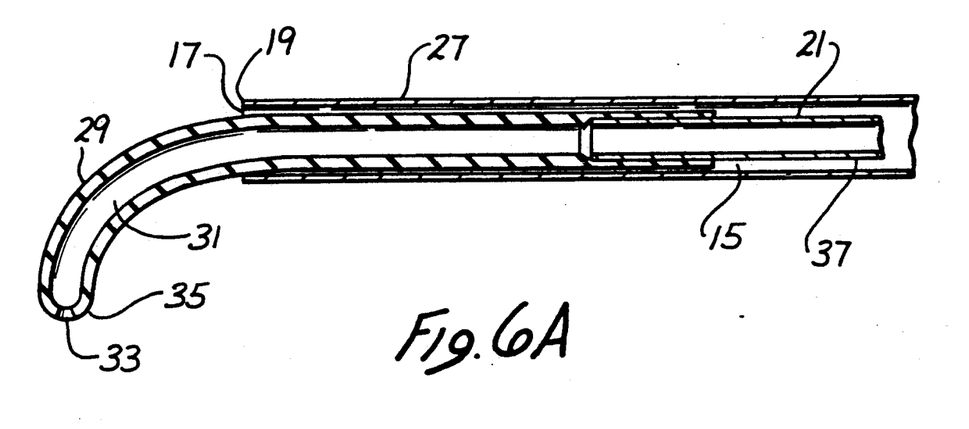
FIG. 6A is a fragmentary sectional view similar to FIG. 6 with the distal end portion of the inner member partially withdrawn into the tube.

The distal end portion 29 can be caused to be in the curved configuration in its unstressed or relaxed condition in various different ways so long as it can be suitably retracted into the passage 15. In this embodiment, the distal end portion 29 is constructed of silicone and is molded into the curved, part-circular configuration shown by way of example in FIG. 6. Accordingly, the length of the arc of the curved configuration which projects from the distal opening 17 can be varied by relatively, longitudinally moving the distal end portions 27 and 29 as shown by comparing FIGS. 2A, 6 and 6A. More specifically, FIG. 2A shows the distal end portion 29 fully retracted into the passage 15, FIG. 6 shows the distal end portion 29 fully extended to provide the maximum length of the inner member distally of the distal portion 27 and FIG. 6A shows the distal end portion 29 partially retracted into the distal end portion 27 to provide a reduced length of arc of the distal end portion 29. Because the distal end portion 27 is linear and rigid, withdrawing of the resilient, normally curved distal end portion 29 into the passage 15 straightens the withdrawn region of the distal end portion 29 (FIG. 2A).

Although the distal end portion 29 can have any desired curved configuration, in this embodiment, the curved configuration is part circular. Although the curved configuration may extend through any desired angle, in this embodiment it extends through an angle X (FIG. 6) of about 250 degrees in the fully extended and relaxed condition. For example, the distal end portion 29 may have an outside diameter of from about 0.025 inch to about 0.065 inch, and the distal end portion 27 may have an outside diameter of about 0.074 inch.

In this embodiment, the inner member 21 is tubular and has an elongated passage 31 (FIGS. 6, 6A) which opens at a distal opening 33 at a distal end 35 of the inner member. As explained more fully hereinbelow, the passage 31 communicates with the proximal opening 23 of the handpiece proximal end 25. In this embodiment, the passage 31 and the distal end portion 29 have circular cross sections, although other cross sections may be employed, if desired.

The inner member 21 includes a main body 37 (FIG. 2A), which is preferably constructed of a rigid material, such as a metal. The main body 37 is suitably attached to the proximal end of the distal end portion 29 as by insertion of a distal region of the main body into the passage 31 (FIG. 6A) and adhering these two members together as by the use of a suitable adhesive. As described more fully hereinbelow, the inner member 21 can be moved longitudinally in the passage 15 and rotated in the passage 15 relative to the distal end portion 27.

The handpiece 13 includes a tip section 39 which includes the distal end portion 29 (FIGS. 1–3); a connector section 41 threaded into the proximal end portion of the tip section 39; a guide 43 suitably coupled to the connector section 41 as by an adhesive; a slider 45 slidably mounted on the guide 43; a barrel 47 adhered, or otherwise suitably attached, to the guide 43; and a connector manifold 49 rotatably coupled to the proximal regions of the barrel 47 in any suitable manner, such as by an annular rib 51 (FIG. 5) on the manifold 49, and an annular mating groove 53 on the barrel 47 which slidably receives the rib 51. The rib 51 can be snap-fit into the groove 53 to mount the connector manifold for rotation about a rotational axis which is coincident with the longitudinal axis of the instrument 11. Rotation of the barrel 47 rotates the guide 43, the slider 45 and the inner member 21 relative to the distal end portion 27 and the connector manifold 49. The handpiece 13 also includes an annular front seal 55 (FIGS. 2, 2A) suitably retained in the connector section 41 and slidably, sealingly receiving the inner member 21, and a back seal 57 (FIGS. 2 and 5) received in a proximal recess of the barrel 47.

As best seen in FIG. 2A, the inner member 21 is spaced radially inwardly from the handpiece 13 to provide a gap which defines a nominally annular fluid path 59 which extends from the distal opening 17 proximally through the tip section 39, the connector section 41 and a port 61 in the front seal 55 to a passage section 63 which extends longitudinally through the guide 43. A longitudinal passage section 65 (FIGS. 2 and 5) in the barrel 47 extends from the passage section 63 proximally to an annular groove 67 near the proximal end of the barrel. The groove 67 communicates through any one of a plurality of apertures 69 in the back seal 57 with a similar groove 71 at the distal end of the connector manifold 49, and a passage section 73 extending through the connector manifold 49 leads to a proximal opening 75. In this manner, the proximal opening 75 communicates with the fluid path 59 which leads to the distal opening 17. Accordingly, by coupling the proximal opening 75 to an irrigation fluid source 77 (FIG. 1) via a flexible conduit 79, irrigation fluid can be supplied through the instrument 11 to the distal opening 17.

The grooves 67 and 71 and the connecting apertures 69 allow fluid communication to be continuously provided between the proximal opening 75 and the distal opening 17 regardless of the relative rotational position of the barrel 47 and the connector manifold 49. In use of the instrument 11, the barrel 47 can be rotated while the connector manifold 49 is allowed to remain stationary as shown by the arrow in FIG. 1 so that the flexible conduits 79 and 91 will not become twisted.

Figure 3:
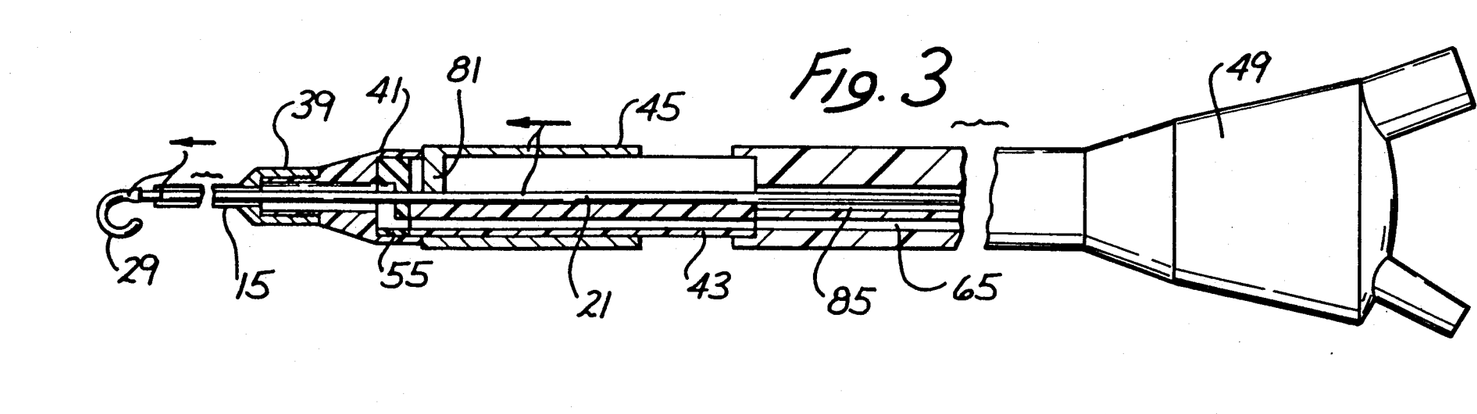
FIG. 3 (sheet 3 of the drawings) is a view partially in section and similar to FIG. 2 with the distal end portion of the inner member extended.
Figure 4:
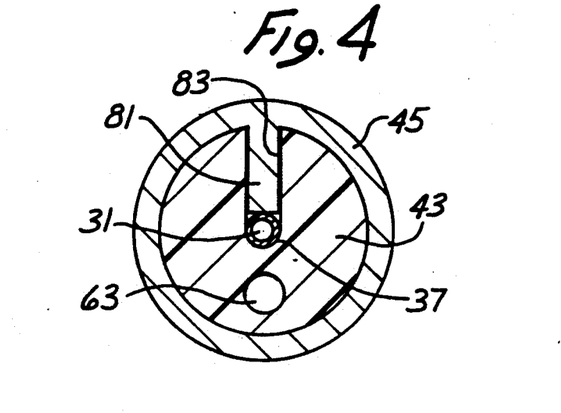
FIG. 4 is an enlarged, sectional view taken generally along line 4—4 of FIG. 2.

The inner member 21 extends proximally through the front seal 55, and the main body 37 thereof is brazed (assuming the use of metal parts) to a tab 81 (FIGS. 2, 2A and 4) of the slider 45. The slider 45 is movable longitudinally on the guide 43, and the tab 81 is received in, and slidable longitudinally in, an axially extending slot 83 of the guide 43. The slide 45 is exposed for manual manipulation as shown in FIGS. 1–3 so the physician can easily move it longitudinally of the handpiece 13. Because the tab 81 is coupled to the main body 37 of the inner member 21, movement of the slider 45 moves the inner member 21 to extend and retract the distal end portion 29. More specifically, the slider 45 is movable between a retracted position (FIGS. 2 and 2A) in which it abuts the barrel 47, and the distal end portion 29 is withdrawn within the passage 15 to an extended position (FIG. 3) in which the tab 81 abuts the connector section 41, and the distal end portion 29 is fully extended from the passage 15.

The inner member 21 also includes a back tube 85 (FIGS. 2 and 5) which is suitably affixed, as by brazing, to the proximal end of the main body 37. The portion of the inner member 21 represented by the back tube 85 also moves with the slider 45.

Figure 5:
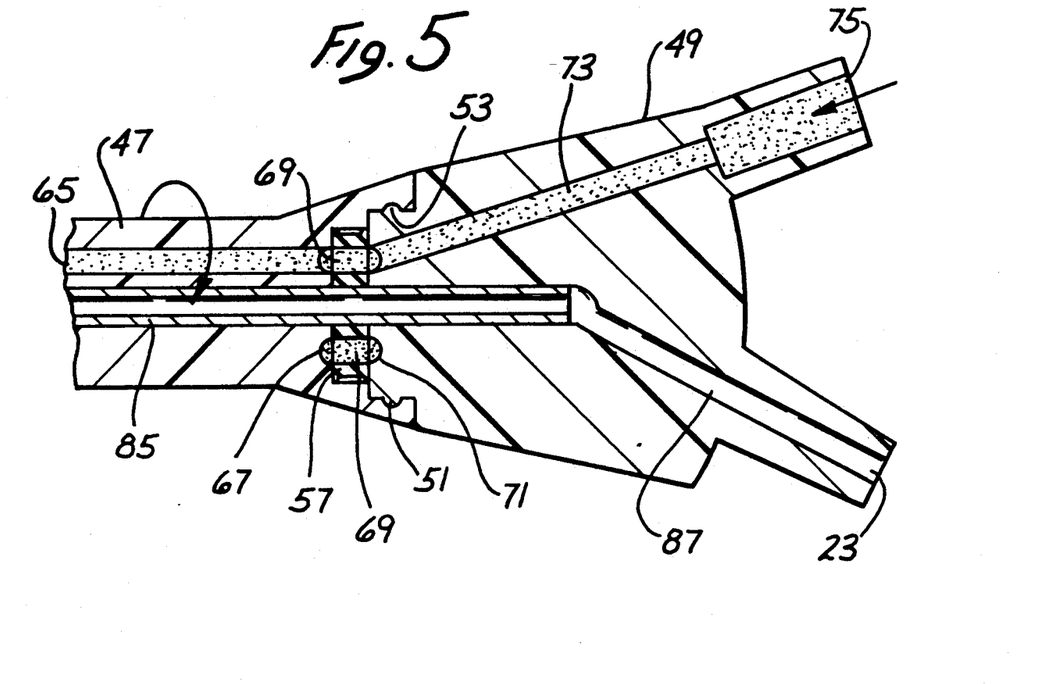
FIG. 5 is an enlarged, fragmentary, sectional view showing the proximal regions of the ophthalmic instrument with the barrel rotated 180° relative to the connector manifold from the position of FIG. 2.

With this construction, the passage 31 of the inner member extends from the distal opening 33 through the distal end portion 29, the main body 37 and the back tube 85 to a passage section 87 (FIGS. 2 and 5) in the connector manifold 49 which leads to the proximal opening 23. Accordingly, by coupling of the proximal opening 23 to a vacuum source 89 (FIG. 1) via a flexible conduit 91, vacuum can be applied to the passage 31 and the distal opening 33 to permit the instrument 11 to be used as an aspirator within the eye. The back tube 85 extends through the back seal 57 as shown in FIG. 5 and is slidable in the seal so that a seal is maintained around the back tube when the inner member 21 is in the fully retracted and fully extended positions.

In a cataract condition, the natural lens of the eye becomes hard, and this hardening typically begins at the center of the lens. To remove the natural lens of the eye, the central hard material is first removed using conventional techniques, such as ultrasound. This leaves the softer peripheral portions of the natural lens within the capsular bag 93 (FIG. 1). The instrument 11 is then inserted through a small incision 95, which may be about 2.2 mm in length, into the eye with the distal end portion 29 being in the retracted position of FIGS. 2 and 2A. The distal end 19 may be inserted into the capsular bag 93, and the distal end portion 29 is advanced to the extended position of FIGS. 1 and 6, or to any of a range of partially extended positions as exemplified by FIG. 6A. Irrigation fluid is supplied by the irrigation fluid source 77, and the vacuum source 89 is initiated to commence the aspiration operation to remove the softer peripheral portions of the natural lens and fractured pieces from central regions of the lens. By varying the length of the distal end portion 27 inserted into the eye, the length of the distal end portion 29 that projects from the distal end 19 and the angle of the distal end portion 29 about the longitudinal axis of the instrument, all of the regions within the capsular bag 93 can be reached through the incision 95 for irrigation and aspiration without significantly moving the distal end portion 27 relative to the eye.

Figures 7, 7B:
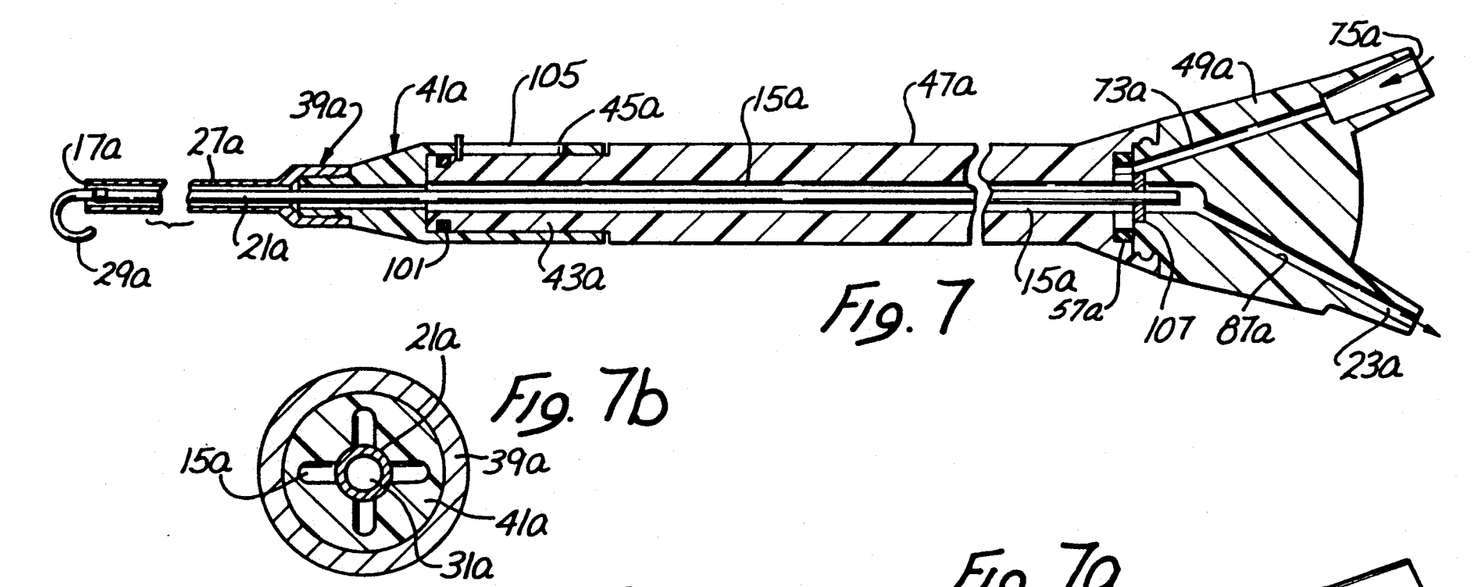
FIG. 7 is a view partially in section and similar to FIG. 3 showing a second form of the invention.
FIG. 7B is a sectional view taken generally along lines 7B—7B of FIG. 7A.
Figure 7A:
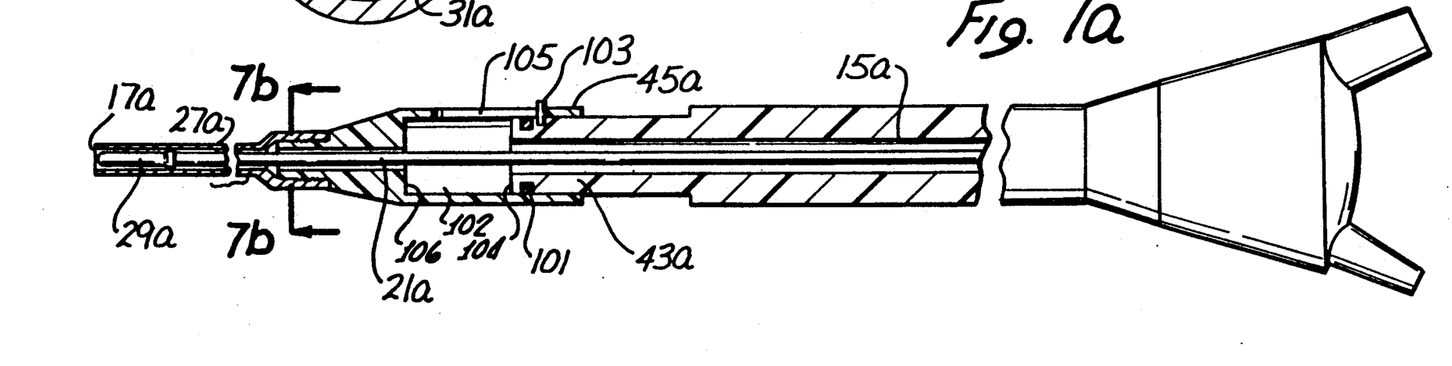
FIG. 7A is a view similar to FIG. 7 with the distal end portion of the inner member fully retracted within the end piece.

FIGS. 7, 7A and 7B show an instrument 11a which is identical to the instrument 11 in all respects not shown or described herein. Portions of the instrument 11a corresponding to portions of the instrument are designated by corresponding reference numerals followed by the letter "a."

Functionally, the instrument 11a is identical to the instrument 11, except for the manner in which the normally curved, resilient distal end portion 29a is moved between the extended position of FIG. 7 and the retracted position of FIG. 7A. Specifically, in the embodiment of FIGS. 7-7B, the distal end portion 29a is moved from the extended position of FIG. 7, to the retracted position of FIG. 7A by moving the distal end portion 27a over the distal end portion 29a.

To accomplish this, the slider 45a is made integral with, or connected to, the connector section 41a and the barrel 47a is made integral with, or connected to, the guide 43a. The slider 45a is mounted for manual longitudinal movement on the guide 43a between the positions of FIGS. 7 and 7A, and a seal 101 carried by the guide 43a seals the interface between the slider 45a and the guide 43a. The extent to which the slider 45a can be moved to the left as viewed in FIG. 7A can be limited in any suitable manner, such as by a pin 103 carried by the guide 43a and riding in a slot 105 of the slider 45a. The maximum amount that the slider 45a can be moved to the right as viewed in FIG. 7 can be limited by the pin 103 and the slot 105 and/or by the engagement of the connector section 41a with the distal end of the guide 43a.

In this embodiment, the inner member 21a is not movable axially with respect to the barrel 47a and is held against longitudinal movement by a retainer and seal 107 attached to the connector manifold 49a. With this construction, suction can be applied through the proximal opening 23a, the passage section 87a, and the inner member 21a. In this embodiment, the back tube 85 of the embodiment of FIGS. 1-6 is eliminated. The suction path is straight and unobstructed for the entire length of the handpiece, except for a bend in the proximal end 25a of the handpiece. Similarly, the irrigation fluid path is straight and unobstructed for its entire length except for the manifold 57a and the bend at the manifold.

The barrel 47a can be rotated relative to the connector manifold 49a in the same manner as in the instrument 11, and the seal 57a allows the passage section 73a to communicate with the passage 15a regardless of the angular orientation of the barrel 47a relative to the connector manifold 49a. Accordingly, an irrigation fluid can be supplied through the proximal opening 75a, the passage section 73a and the passage 15a to the distal opening 17a. In this regard, the inner member 21a does not completely fill the passage 15a so that there is an annular flow path for the irrigation fluid. As shown in FIG. 7B, the passage 15a is preferably in the shape of a plus or cross to provide support for the inner member 21a as the connector section 41a is slid over the inner member.

Figure 8:
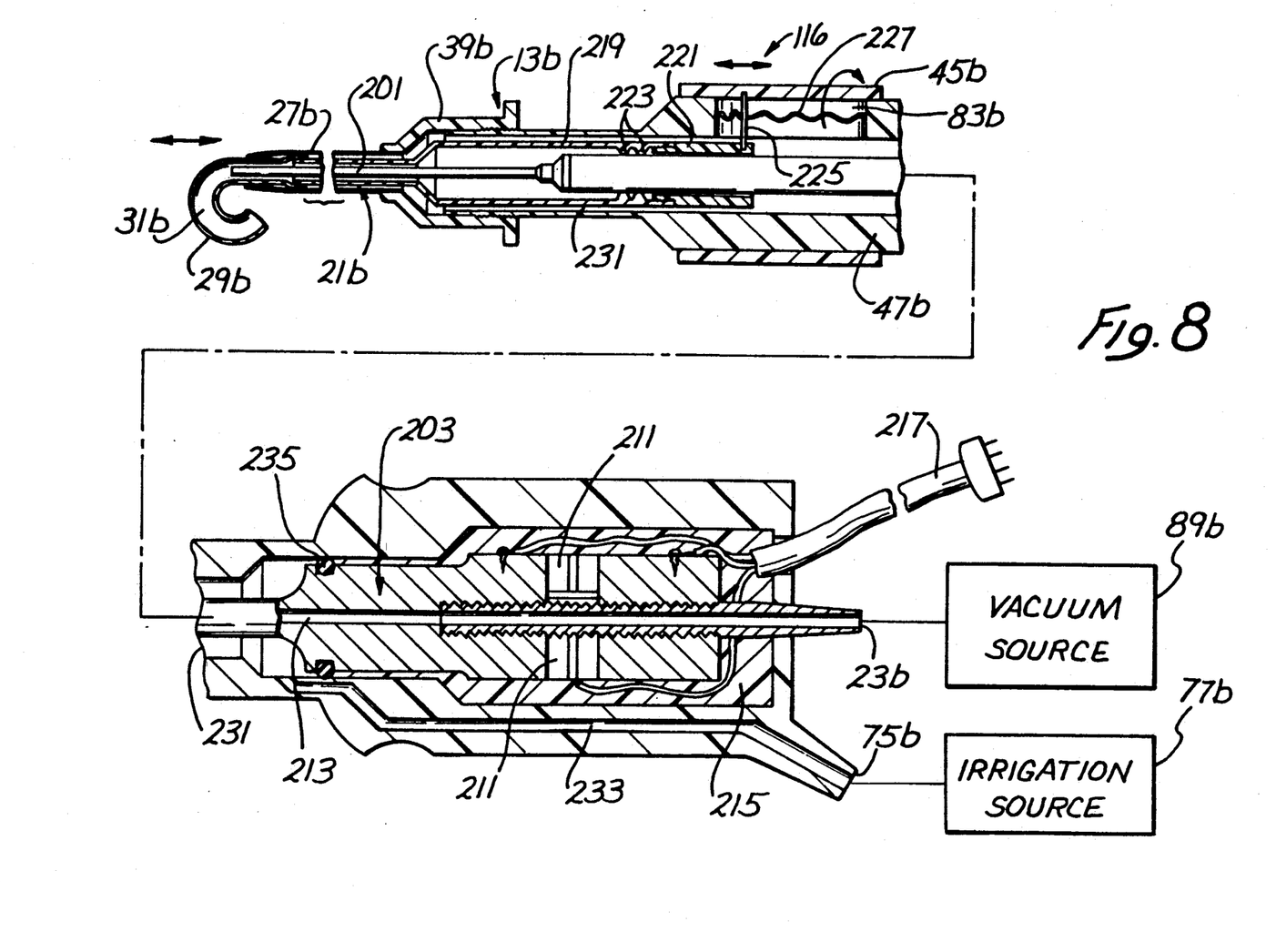
FIG. 8 is a fragmentary, longitudinal sectional view illustrating a third form of ophthalmic instrument which includes an ultrasound needle. The distal end portion of the inner member is shown in the extended position.
Figure 9:
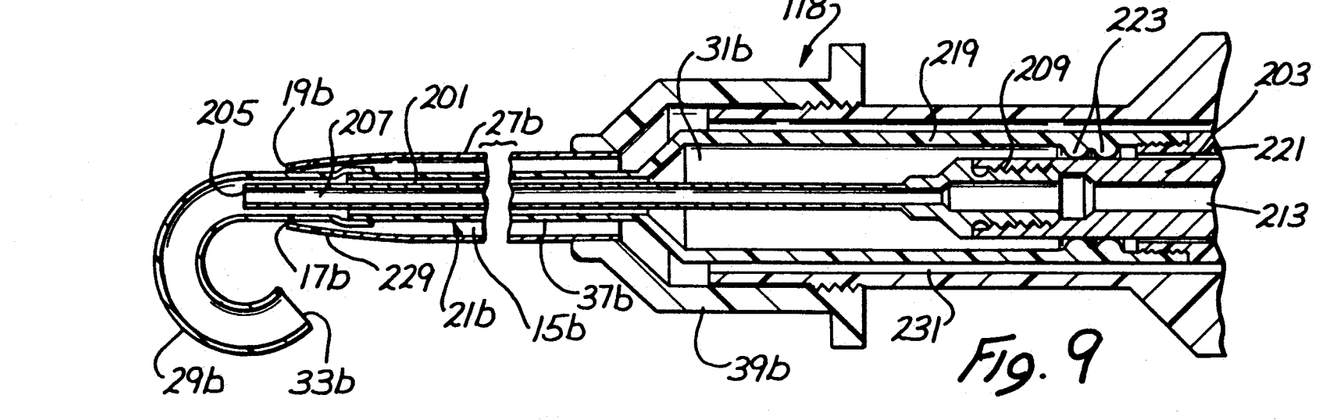
FIG. 9 is an enlarged, fragmentary sectional view of a distal portion of the instrument of FIG. 8.
Figure 9A:
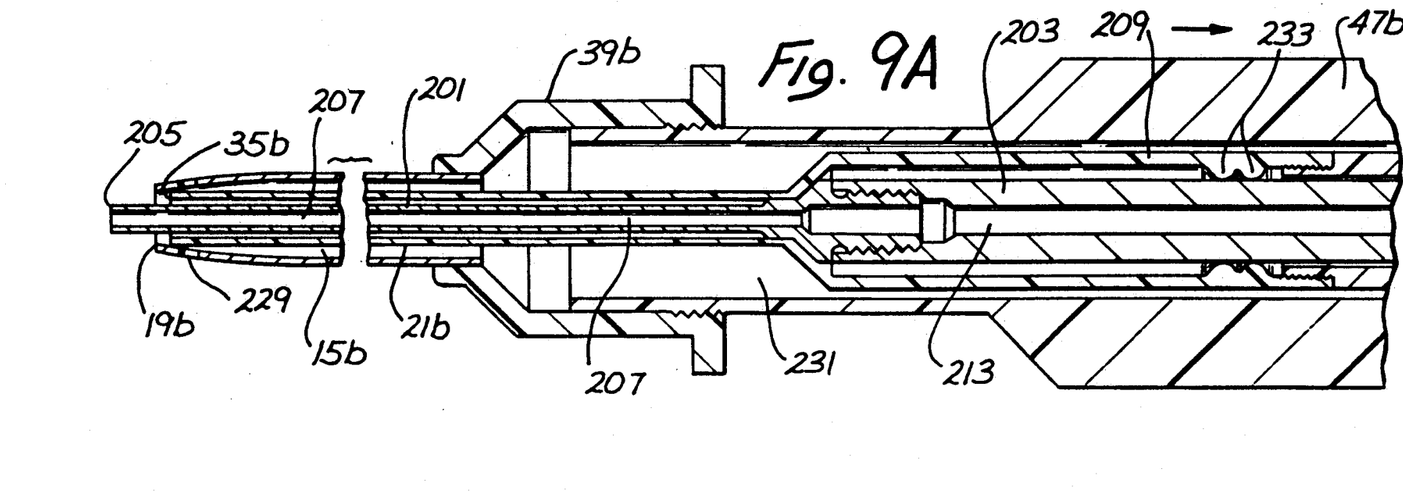
FIG. 9A is an enlarged, fragmentary sectional view similar to FIG. 9 showing the distal end portion of the inner member retracted to expose the distal tip of the ultrasound needle.

FIGS. 8, 9 and 9A show an instrument 11b which is identical to the instrument 11 in all respects not shown or described herein. Portions of the instrument 11b corresponding to portions of the instrument 11 are designated by corresponding reference numerals followed by the letter "b."

The primary difference between the instruments 11 and 11b is that the latter includes an ultrasound needle 201 and an ultrasound horn 203 to impart ultrasonic energy to the ultrasound needle. The ultrasound needle 201 is tubular (FIG. 9) and has a distal end 205 and an elongated needle passage 207 opening at the distal end 205. A distal end portion of the ultrasound needle 201 projects out of the distal opening 17b of the distal end portion 29b.

The ultrasound needle 201 is coupled to the horn 203 by screw threads 209 (FIG. 9). The ultrasound horn 203 includes ultrasound drivers 211 (FIG. 8) which impart ultrasound energy to the horn 203. The passage 207 communicates with an axial passage 213, which extends completely through the ultrasound horn 203 and is coupled to a vacuum source 89b which applies a suction force to the needle passage 207 (FIG. 9) via the passage 213 which tends to pull material into the distal end 205 of the ultrasound needle 201. The ultrasound horn 203 is suitably retained within the handpiece 13b as by potting 215 (FIG. 8). Electrical energy is applied to the horn 203 by means of an electrical conduit 217.

The inner member 21b includes the normally curved, resilient and flexible distal end portion 29b, which may be substantially identical to the flexible and resilient distal end portion 29 in FIG. 6, and a relatively rigid main body 37b attached to the distal end portion 29b and having an enlarged section 219 (FIG. 9) threadedly attached to an extension 221. The main body 37b may be constructed of a stiff polymeric material, such as urethane. The passage 31b is enlarged within the enlarged section 219, and annular seals 223, which may be integral with the enlarged section 219, form a seal between the enlarged section and a region of the ultrasound horn 203 as best shown in FIG. 9.

As with the instrument 11, the inner member 21b can be moved between a first or extended position in which the distal end portion 29b of the inner member 21b extends distally of the distal end portion of the ultrasound needle 201 as shown in FIGS. 8 and 9 and a second or retracted position in which the distal end portion of the ultrasound needle projects distally of the distal end of the inner member as shown in FIG. 9A. Although this movement of the inner member 21b can be brought about in different ways, in this embodiment, this is accomplished by the slider 45b (FIG. 8) which is coupled to the extension 221 by a coupling member 225 which extends through a bellows seal 227 in the slot 83b of the barrel 47b of the handpiece 13b. Accordingly, by manually moving the slider 45b axially on the barrel 47b, the inner member 21b is directly driven by the coupling member 225 between the positions of FIGS. 9 and 9A. This causes motion of the inner member 21b relative to both distal end portion 27b of the handpiece and the distal end portion of the needle. Thus, either or both the end portions 27b and the needle end portion operate to control the curvature of the flexible end portion 29b of the inner member. The bellows seal 227 prevents any fluid leakage out through the slot 83b. The seals 223 seal the interface between the enlarged section 219 of the inner member and the ultrasound horn 203 as the inner member is moved between the extended and retracted positions.

The handpiece 13b includes a two-piece tip section 39b, with the distal end portion 27b being tapered radially inwardly adjacent the distal end 19b. The proximal end of the tip section 39b is threadedly attached to the distal end of the barrel 47b. In addition, the tapered distal ends may have one or more ports 229 which extend to the passage 15b. The passage 15b extends longitudinally of the needle and communicates with a central axial passage 231 extending through a major length of the barrel 47b. This passage communicates with a passage section 233 (FIG. 8) in the barrel extending between the passage 231 and the proximal opening 75b which is coupled to the irrigation source 77b. With this construction, an irrigation fluid can be supplied from the source 77b through the proximal opening 75b, the passage section 233, the passage 231, and the ports 229 to the interior of the eye. An annular seal 235 (FIG. 8) prevents leakage of the irrigation fluid proximally, and the bellows seal 227 prevents leakage of this fluid out through the slot 83b. Finally, the seals 223 prevent leakage of this fluid into the passage 31b.

In use, the distal end portion 27b is advanced through a small incision into the interior of the eye with the inner member 21b in the retracted position of FIG. 9A. Within the eye, the ultrasound drivers 211 are energized to drive the ultrasound needle 201 to break up the hard nucleus of the natural lens. Irrigation fluid can be applied as desired in a longitudinal path along the inner member, through the ports 229, and vacuum can be applied through the passage 207 of the ultrasound needle 201 to remove the particulate matter and the fluid. When desired, the inner member 21b can be moved to the extended position of FIG. 9 and used as described above in connection with the instrument 11 for aspiration purposes. However, the instrument 11b does not provide for rotation of the inner member 21b relative to any portion of the handpiece 13b. Rather, to rotate the distal end portion 29b, the entire handpiece 13b is rotated. In addition, the suction force is applied through the needle passage 207 and then through the distal end portion 29b to the distal opening 33b. Also, the distal opening 33b is larger than the distal opening 33 of the instrument 11 so that larger particles can be drawn into the passage 31b. The seals 223 sealingly engage the ultrasound horn 203 to prevent loss of vacuum pressure proximally of the seals.

Figure 10:
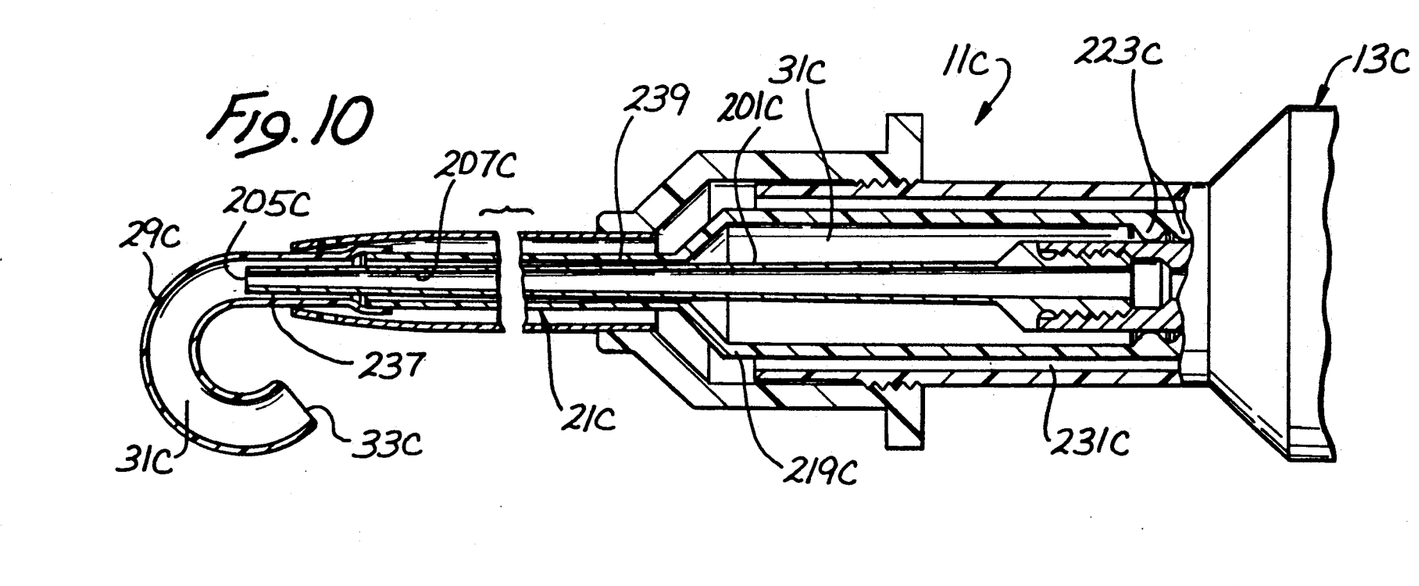
FIG. 10 (sheet 3 of the drawings) is an enlarged, fragmentary, sectional view similar to FIG. 9 showing a fourth embodiment of the invention.
Figure 11:
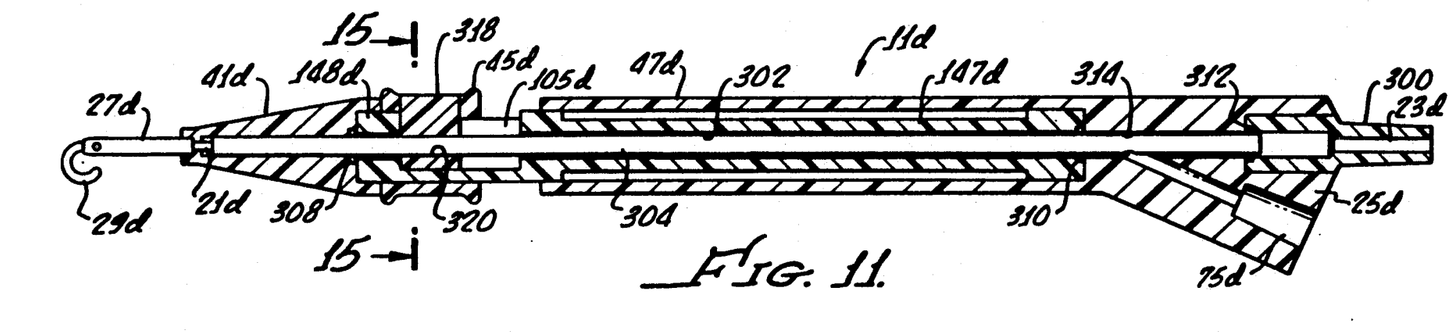
FIG. 11 is a longitudinal sectional view of still another embodiment of the invention.

FIG. 10 shows an instrument 11c which is identical to the instrument 11b in all respects not shown or described herein. Portions of the instrument 11c corresponding with portions of the instrument 11b are designated by corresponding reference numerals followed by the letter "c."

The instrument 11c differs from the instrument 11b in that the ultrasound needle 201c has an elongated, tapered needle passage 207c which is of progressively increasing cross-sectional area as the ultrasound needle passage extends proximally of the distal end 205c. This feature reduces the likelihood that debris being sucked through the needle passage 207c will become entrapped in the passage and block it.

Another difference is that the ultrasound needle 201c has an outer periphery 237 which is tapered and which is of progressively increasing cross-sectional area as it extends from the distal end 205c proximally to a location 239. The outer periphery 237 is engageable with the inner member 21c at the location 239 in the extended position of the inner member to form a seal at the location 239. The seal formed at the location 239 serves as a secondary or backup seal to the seals 223c which prevent leakage of the irrigation fluid distally into the passage 31c and out of the distal opening 33c. Between the location 239 and the enlarged section 219c, the outer periphery 237 may be of constant diameter or of slightly reduced diameter to allow movement of the inner member 21c over the ultrasound needle 201c between extended and retracted positions. If the diameter of the outer periphery 237 is maintained constant from the location 239 proximally, then the seal at the location 239 is maintained in both the extended and retracted positions of the inner member 21c. On the other hand, if the diameter of the outer periphery 237 is slightly reduced proximally of the location 239, then the seal would not exist when the distal end portion 29c is in the retracted position.

Of the several embodiments illustrated, that shown in FIGS. 7, 7A and 7B has certain advantages that make this embodiment more readily adaptable to mass production of an inexpensive, disposable instrument. These advantages include the relatively simple configuration of the parts, the straight through flow paths, and increased efficiency and low cost of manufacture, all of which are particularly useful in the described disposable instrument. However, in the arrangement of FIG. 7, flow of irrigation fluid may be subject to unwanted variation when the slider 45a and connection section 41a are moved back and forth to change the curvature of the distal end portion 29a. As can be seen in FIG. 7A, a cavity 102 exists between the rear facing shoulder 106 of connection section 41a and the forward facing end 104 of the barrel guide portion 43a. This area 102 is filled with irrigation fluid during use of the device for irrigation. During retraction of the slider, that is, as it is moved from the position of FIG. 7A toward the position of FIG. 7, the cavity 102 is caused to decrease in volume. This dynamic decrease in volume tends to create an increased pressure pulse in the irrigation fluid. On the other hand, as the slider 45a and connector section 41a are extended to move from the position of FIG. 7 toward the position of FIG. 7A, the cavity 102 dynamically increases in volume so that irrigation fluid flowing in the barrel passage 15a tends to flow into and fill up the increasing volume of cavity 102. This causes a decreased pressure pulse. A lesser amount of irrigation fluid reaches the eye cavity, or for a short time there may be no irrigation fluid at all that reaches the eye cavity. Thus motion of the slider and connecting section can cause serious unwanted variation in the irrigation fluid flow which may have significant adverse affects on delicate and sensitive eye capsule tissues.

To take advantage of desirable features of the embodiment of FIG. 7A while at the same time avoiding or minimizing the described variation in irrigation fluid flow, an instrument is constructed in the configuration illustrated in FIGS. 11-15. These figures show an instrument 1d which is identical to the instrument 11 in all respects not shown or described herein. Portions of the instrument 11b corresponding to portions of the instrument 11 are designated by corresponding reference numerals followed by the letter "d". Certain elements of the instrument 11d which have no direct counterparts in the instrument 11 are designated by other reference numerals.

Instrument 11d is most similar to the embodiment shown in FIGS. 7, 7A and 7B, but differs therefrom primarily by a construction that minimizes the variation in the volume of cavity 102d as the normally or naturally curved distal end portion 29d is manipulated to change its curvature. Thus, in the instrument of FIGS. through 13 the handpiece includes a fixed outer barrel portion 47d having a proximal end 25d which is formed with an aspiration fitting 300, having a proximal aspiration opening 23d. Also formed in a laterally inclined part of the proximal end 25d is an inclined proximal opening 75d through which irrigation fluid is applied to the instrument.

Figures 13, 14, 15:
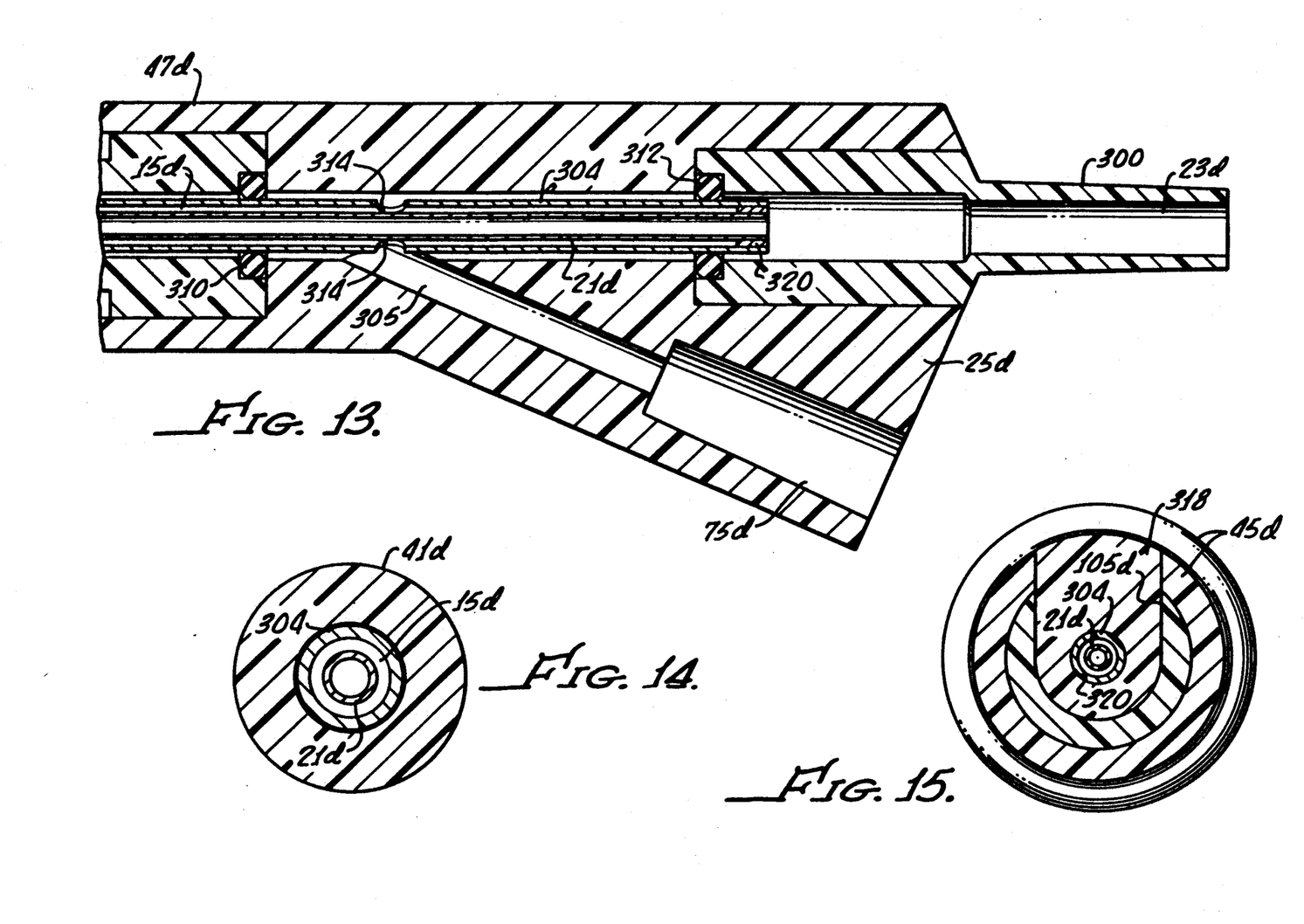
FIG. 14 is a section taken on line 14—14 of FIG. 12.
FIG. 15 is a section taken on line 15—15 of FIG. 11.

Outer barrel 47d is a straight, hollow cylindrical member having an inner barrel portion 147d fixed therein, as by a press fit therein for example. Inner barrel portion 147d includes an integral distal portion 148d that projects distally of the distal end of outer barrel 47d and is formed with a slider receiving slot 105d. Fixed to the distal end 148d of inner barrel 147d is a tapered nose or connecting section 41d that has a distally facing recess in which is fixedly received (by being a press fit) a handpiece distal end sleeve 27d having an irrigation port 17d at its distal end. The inner barrel 147d is formed with a straight through internal bore 302 in which is mounted for longitudinal slidable motion an assembly comprising an inner tube 21d and an intermediate member or tube 304 that is fixed to inner member 21d, as by silver solder 320 (FIG. 13). The tube 304 is concentric with and circumscribes the inner member 21d but has a distal end positioned proximally of the distal end of inner member 21d. Intermediate member or tube 304 has an internal diameter greater than the external diameter of the inner member 21d (see FIG. 14) so as to provide an annular irrigation fluid passage 15d therebetween. The internal bore of outer barrel 47d is provided with a plurality of longitudinally spaced sealing o-rings 310 and 312 that cooperate with an o-ring 308 in connecting section 41d to slidably engage the exterior of the intermediate member 304 and to allow slidable motion of the member 304 relative to the handpiece barrel portions while providing fluid sealing of the small space provided between the inner barrel and the intermediate member.

A plurality of circumferentially spaced apertures 314 are formed in a proximal end of intermediate member 304 (FIG. 13) adjacent the distal end 305 of the irrigation opening 75d to permit passage of irrigation fluid from the passage 75d, through the apertures 314 and into the annular irrigation passage 15d. O-rings 310 and 312 are formed on opposite sides of the apertures 314 to provide for sealing of fluid flowing from the irrigation opening 75d throughout the range of longitudinal motion of intermediate tube 304. Thus the annular space between o-rings 310,312 and between the handpiece barrel 47d and member 304 forms an irrigation fluid manifold from which fluid flows into passage 15d through openings 314.

Slot 105d (FIGS. 11 and 15) in the portion 148d of inner barrel 147d at the proximal end of connector section 41d receives a slider arm 318 having an apertured inner portion 320 that is fixedly connected (as by being a press fit, for example) to the intermediate member 304. Arm 318 extends radially outwardly through slot 105d for fixed connection to a finger operated slider 45d that is slidably mounted to the exterior of the distal end portion 148d of inner barrel 147d.

It will be seen that moving slider 45d back and forth longitudinally relative to the handpiece barrel 147d will longitudinally shift the assembly of mutually fixed intermediate tube 304 and inner tube 21d, thereby causing relative motion of the flexible inner tube end portion 29d with respect to the rigid distal end portion 27d that is fixed with respect to the handpiece. Thus, effectively, motion of the slider causes the naturally curved flexible distal end portion of the inner member 21d to change its curvature as the curved portion is caused to move into and out of the distal end sleeve 27d through its irrigation port 17d.

Figure 12:
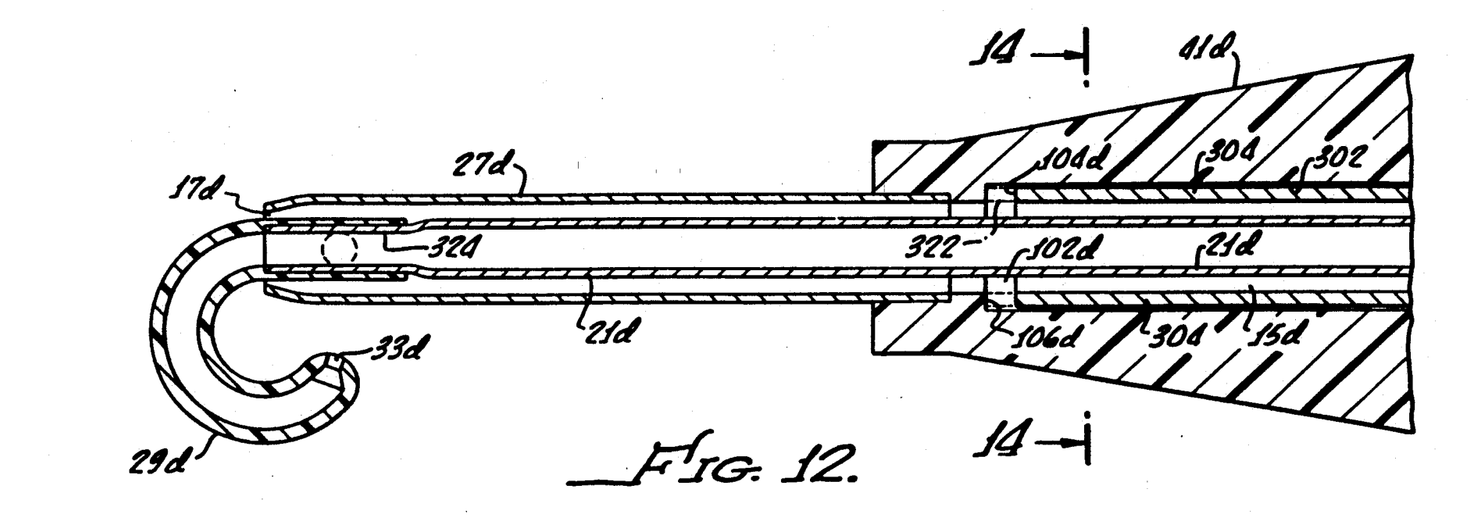
FIGS. 12 and 13 are enlarged longitudinal sectional views of distal and proximal portions of the embodiment of FIG. 11.

In the course of this motion end portion 104d (FIG. 12) of the intermediate member 304 acts as a very small area piston that will effect a small change in volume of cavity 102d only over a small tubular volume 322 shown in dotted lines in FIG. 12. This small tubular volume has a thickness equal to the thickness (0.020 inches) of the wall of the intermediate member 304 and a length equal to the longitudinal distance of reciprocal motion of the slidable assembly of inner and intermediate tubes. Therefore, the net change in volume of cavity 102d is minimized, with the concomitant avoidance of adverse affects of variation in irrigation fluid flow.

In an exemplary mechanization of the arrangement of FIGS. 11 through 15, the inner tube 21d has an outer diameter of about 0.0425 inches and a wall thickness of about 0.0150 inches. The intermediate member 304 has an inner diameter of about 0.063 inches and an outer diameter of about 0.083 inches, with a wall thickness of 0.020 inches. Thus, the radial irrigation fluid gap is 0.021 inches. At its proximal end portion the intermediate member 304 is fixed to the proximal end of the inner member by a suitable adhesive or other means, such as silver solder 320. No other interconnection between the inner member 21d and intermediate member is needed. In an exemplary mechanization the handpiece inner barrel 147d has an inside diameter to closely but slidably fit the exterior surface of the intermediate member. Inner tube 21d is formed of a rigid stainless steel from its proximate end to a reduced diameter distal end portion 324 to which is attached the previously described flexible plastic end portion 29d having a curved shape in relaxed condition and having a suction opening 33d in its tip. Intermediate member 304 is also made of stainless steel. Handpiece barrel 147d, including tapered connecting section 41d, are made of a rigid molded ABS plastic and the distal end sleeve 27d of the handpiece is formed of urethane bonded or press fit to the distal end of the connection section 41d.

Importantly, the very small wall thickness (0.020 inches) of intermediate member 304 causes this member to have a very small area of its distal end 104d. Distal end 104d is spaced proximally of the proximal end of connecting section 41d to permit the longitudinal sliding of the tube 304 relative to the handpiece body. It is the distal end 104d of intermediate member 304 that acts as a piston within cavity 102d so as to change volume of the cavity only through the very small volume 322 as the slidable assembly of the intermediate member 304 and inner member 21d is moved back and forth longitudinally of the handpiece to change curvature of the tip 29d.

As in the embodiment of FIGS. 7-7b, the suction and irrigation fluid flow paths are straight and unobstructed through the major portion of the length of the handpiece.

The instrument of FIGS. 11 through 15 is used in the same manner as described in connection with the other embodiments disclosed herein. The flexible distal end portion 29d of the inner tube has its curvature changed while the instrument is in the eye cavity. This is accomplished merely by moving the finger operated slider 45d from a fully retracted position, in which the curved distal end portion 29d is substantially straight for insertion into the cavity, to any one of a number of forwardly displaced positions in which the flexible distal end portion extends different amounts beyond the distal end of the distal end sleeve 27d of the handpiece. Rotation of the distal end portion 29d is accomplished by rotation of the entire handpiece. Effectively, the configuration of FIGS. 11 through 15 enables movement of both the irrigation flow path and the aspiration flow path independently of the instrument body 47d, whereby irrigation fluid flow path volume changes are minimized. The reduced diameter section 324 of inner member 21d enables the outer surface of the flexible end portion 29d to be flush with the outer surface of inner member 21d to avoid possible interference with the distal end of sleeve 27d as the two are slidably moved relative to one another.

Although exemplary embodiments of the invention have been shown and described, many changes, modifications and substitutions may be made by one having ordinary skill in the art without necessarily departing from the spirit and scope of this invention.

I claim:

1. An ophthalmic instrument comprising:
   an elongated tube having proximal and distal end portions, and an elongated passage opening at a distal opening at the distal end portion;
   an elongated inner member having a resiliently deformable distal end portion which has a curved configuration in relaxed condition and is sized to be received through an incision into the eye, said distal end portion of the inner member being capable of performing a function within an eye, said inner member being at least partially received in the elongated passage of the tube;
   a handpiece including a barrel having a longitudinal bore, said tube being slidably received within said bore and being fixedly connected to said inner member; and
   means for causing relative longitudinal movement between said handpiece barrel and at least said inner member to change the configuration of said deformable distal end portion.

2. The instrument of claim 1 wherein said elongated tube is formed of a thin walled tube, wherein said distal end portion of said tube is within said bore, and wherein said handpiece has a distal end portion, extending distally beyond said tube distal end portion.

3. The instrument of claim 1 wherein said barrel includes a distal end portion having an opening, said flexible distal end portion of said inner member being slidably received in said opening.

4. The instrument of claim 1 wherein said inner member and said elongated tube are radially spaced from one another an annular gap therebetween, and means for flowing irrigation fluid though said gap.

5. The instrument of claim 1 wherein said barrel includes a distal end portion having a second bore in communication with said first mentioned bore, said second bore having a diameter less than the diameter of said first mentioned bore, said tube and said inner member being spaced from one another to provide a gap through which irrigation fluid may flow, said gap being in communication with said second bore, and wherein said tube is formed of a thin walled tube to minimize fluid volume changes in irrigation flow paths during said relative longitudinal movement.

6. An ophthalmic instrument comprising:
   a handpiece having a distal end portion, a distal end and an elongated passage opening at a distal opening at the distal end;
   said distal end portion being sized to be received through an incision into the eye;
   an intermediate tube slidably mounted within said elongated passage and having a distal end spaced proximally of said handpiece distal end;
   an elongated inner member having a resiliently deformable distal end portion which has an arc of curved configuration in a relaxed condition adapted to project from said distal opening;
   said distal end portion of the inner member being sized to be received through an incision into the eye, and being capable of performing a function within an eye;
   said inner member being mounted within said tube for longitudinal motion therewith relative to said distal opening to cause the deformable distal end portion of the inner member to project through the distal opening a variable amount to change the length of the arc of the curved configuration projecting from the distal opening;
   said inner member having a distal end and an elongated passage opening at said distal end of the inner member; and
   means fixed to said tube and slidable relative to the handpiece for moving the inner member relative to the handpiece.

7. The instrument of claim 6 wherein said tube cooperates with the inner member and is fixed thereto for defining a fluid flow path from a proximal end of said handpiece to said handpiece distal end portion.

8. The instrument of claim 6 wherein said means for moving the inner member comprises a slider connected to said tube, said inner member being fixed to and positioned within said tube and cooperating therewith to define a fluid flow path.

9. The instrument of claim 8 wherein said handpiece has a proximal end portion, and including a suction fitting in the proximal end portion of said handpiece in communication with said elongated passage of said inner member.

10. The instrument of claim 9 wherein said handpiece includes an irrigation fluid opening, and sealing means between said handpiece and said tube for defining an irrigation fluid manifold in communication with said irrigation fluid opening.

11. The instrument of claim 10 including a plurality of apertures in said tube in communication with said manifold.

12. An ophthalmic instrument comprising:
   a handpiece having a distal end portion and an elongated passage opening at a distal opening at the distal end portion;
   a hollow elongated inner member having a resiliently deformable distal end portion which has a curved configuration in a relaxed condition;
   an intermediate member slidably mounted within the elongated passage of said handpiece and having an intermediate bore, said elongated inner member having a portion thereof received in the bore of said intermediate member and being fixed thereto; and
   means for slidably shifting said intermediate member and said inner member relative to said handpiece to relatively shift said deformable distal end portion of said inner member relative to the distal end portion of said handpiece.

13. The instrument of claim 12 wherein said distal end,/portion of said handpiece and a portion of said inner member define a distal irrigation fluid flow path, and wherein said intermediate member is spaced from said inner member to define a proximal irrigation fluid flow path in communication with said distal fluid flow path.

14. The instrument of claim 12 wherein said intermediate tube is a thin wall tube.

* * * * *